United States Patent

Manthrop et al.

[11] Patent Number: 5,916,217
[45] Date of Patent: Jun. 29, 1999

[54] CRANIAL SPRING CLIP

[75] Inventors: John H. Manthrop, Downingtown, Pa.; James P. Hearn, Claymont, Del.; William S. Schnorr, Philadelphia, Pa.

[73] Assignee: Synthes (USA), Paoli, Pa.

[21] Appl. No.: 09/003,332

[22] Filed: Jan. 6, 1998

[51] Int. Cl.$^6$ .................................................. A61B 17/84
[52] U.S. Cl. ................... 606/72; 606/73; 606/69
[58] Field of Search .................... 606/69, 70, 72, 606/75, 86, 104, 151; 29/243.56; 411/61, 508

[56] References Cited

U.S. PATENT DOCUMENTS

| | | | |
|---|---|---|---|
| 2,319,059 | 5/1943 | Hansman | 411/508 |
| 2,509,192 | 5/1950 | Poupitch | 411/508 |
| 2,825,948 | 3/1958 | Parkin . | |
| 3,973,295 | 8/1976 | Janke | 24/73 |
| 3,995,404 | 12/1976 | Thaw et al. | 52/514 |
| 4,651,724 | 3/1987 | Berentey et al. . | |
| 4,762,122 | 8/1988 | Slocum . | |
| 4,800,874 | 1/1989 | David et al. . | |
| 4,852,558 | 8/1989 | Outerbridge . | |
| 4,905,679 | 3/1990 | Morgan | 606/70 |
| 4,923,471 | 5/1990 | Morgan | 623/16 |
| 5,084,944 | 2/1992 | Hileman | 24/453 |
| 5,352,229 | 10/1994 | Goble et al. | 606/72 |
| 5,395,372 | 3/1995 | Holt et al. | 606/61 |
| 5,413,577 | 5/1995 | Pollock | 606/69 |
| 5,425,772 | 6/1995 | Brantigan | 623/17 |
| 5,454,814 | 10/1995 | Comte | 606/75 |
| 5,487,741 | 1/1996 | Maruyama et al. | 606/60 |
| 5,501,685 | 3/1996 | Spetzler | 606/75 |
| 5,527,312 | 6/1996 | Ray | 606/61 |
| 5,549,620 | 8/1996 | Bremer | 606/151 |
| 5,569,250 | 10/1996 | Sarver et al. | 606/69 |
| 5,645,599 | 7/1997 | Samani | 623/17 |
| 5,662,655 | 9/1997 | Laboureau et al. | 606/75 |
| 5,669,912 | 9/1997 | Spetzler | 606/72 |
| 5,800,436 | 9/1998 | Lerch | 606/72 |

FOREIGN PATENT DOCUMENTS

| | | |
|---|---|---|
| 14 05 829 a1 | 1/1958 | U.S.S.R. . |
| 14 91 496 A1 | 4/1958 | U.S.S.R. . |

*Primary Examiner*—Micheal Buiz
*Assistant Examiner*—David O. Reip
*Attorney, Agent, or Firm*—Pennie & Edmonds LLP

[57] ABSTRACT

A cranial spring clip for attaching a bone flap to a skull is disclosed. The clip includes a substantially flat flap clipping portion, a substantially flat skull clipping portion, an extension disposed between, connecting, and substantially perpendicular to the flap clipping and the skull clipping portions, at least one burr attached to the extension, and a fastening element. When the clip is implanted, the topography of the flap clipping and skull clipping portions, the only parts of the clip above the outer table of the skull, provides the clip with a low profile. At least a portion of the extension is resilient in nature so that, the resilient portion flexes inward upon insertion in the saw gap and then flexes back to fix the clip in place. The burr penetrates the skull to also fix the clip in place. As the extension has a length that is shorter than the thickness of the skull and the bone flap, there is minimal possibility of accidental injury to the brain. The fastening element can be located on the extension so that it is substantially perpendicular to the extension when implanted. Alternatively, the fastening element is located on the flap clipping portion so that it is substantially perpendicular to the flap clipping portion. In one embodiment, the extension is substantially flat, while in another, the extension is U-shaped.

19 Claims, 3 Drawing Sheets

CRANIAL SPRING CLIP

FIELD OF THE INVENTION

The present invention is directed to a cranial spring clip for attaching a bone flap to a skull.

BACKGROUND OF THE INVENTION

In craniotomies, access to the cranium is typically achieved by the creation of a hole in the skull. This hole or window is usually created by identifying the area of the brain to which access is needed, drilling several burr holes into the skull near the periphery of this area, inserting a cutting tool into one of the burr holes, and making cuts from one burr hole to another, i.e., connecting osteotomies. Removing the cut-out area of the skull, i.e. the bone flap, provides the desired access to the cranium.

If all of the burr holes are joined by cuts such that the cuts form a complete outline of the window, then the bone flap can simply be removed. Alternatively, if the cuts form only a partial outline of the window, then the bone flap can be bent out of the way. Although the size and shape of the bone flap will vary with the desired cranial access area and size, a typical flap would be generally rectangular in shape and approximately four by six centimeters.

After the desired medical or surgical procedure on the cranium has been performed, the bone flap must be replaced and held in a stable position to allow the skull to heal. Known methods of fixing the bone flap to the skull include drilling pairs of threading holes in the edges of the skull and bone flap, threading wire through the holes, and twisting or tying the ends of the wire together to secure the edges. Disadvantages of this method include the tedious nature and length of time required for the procedure and the possibility of injury to the dura by drilling the threading holes too deep or by the sharp ends of the wires.

Another method of fixation involves the use of bone plates which are secured across the connecting osteotomies by screws. The disadvantages associated with the use of plates and screws relate to the undesirable cosmetic appearance resulting from the protrusion of the plate and screw above the bone surface. As there is minimal intervening soft tissue between the skull and the skin, unappealing external appearance is particularly a problem. The lack of soft tissue also has the unwanted consequence of permitting the patient to feel the plate and screw simply by pressing on the scalp. Thus, there is a need for improved devices for fixing a bone flap to a skull.

SUMMARY OF THE INVENTION

The present invention relates to a cranial spring clip for attaching a bone flap to a skull in a manner that is quick yet minimizes the potential for injury to the brain. Furthermore, this clip has a low profile so that after implantation, undesirable cosmetic appearances are avoided.

The cranial spring clip according to the present invention preferably comprises a flap clipping portion; a skull clipping portion; an extension disposed between, connecting, and substantially perpendicular to the flap clipping portion and the skull clipping portion; and a fastening element. The flap and skull clipping portions are both substantially flat and upon implantation, rest on top of the bone flap and skull, respectively. As a result, the cranial spring clip achieves the desired profile.

When the clip is implanted, the extension fits in the saw gap between the bone flap and the skull. Since at least a portion of the extension is resilient in nature, the resilient portion flexes inward upon insertion in the saw gap and then flexes back. As the extension has a length that is shorter the thickness of the skull and the bone flap, there is minimal possibility of accidental injury to the brain. Connected to the extension is at least one burr. The burr has a tip that extends from the extension at an angle. When the clip is implanted and the extension is positioned in the saw gap, at least the tip of the burr penetrates a side surface of the skull.

The clip has a fastening element which secures the clip to the bone flap. Typically, the fastening element consists of a fastener hole for receiving a fastener such as a screw. The fastener hole can be located on the extension so that the fastener is substantially perpendicular to the extension when implanted. Alternatively, the fastener hole is located on the flap clipping portion so that the fastener is substantially perpendicular to the flap clipping portion.

In a first embodiment, the extension is substantially flat and the resilient portion of the extension is the portion which connects the base of the burr to the extension. In another embodiment, the extension is U-shaped and the resilient portion is the curved section connected the two ends of the extension.

DESCRIPTION OF THE PREFERRED EMBODIMENTS

Figure 1:
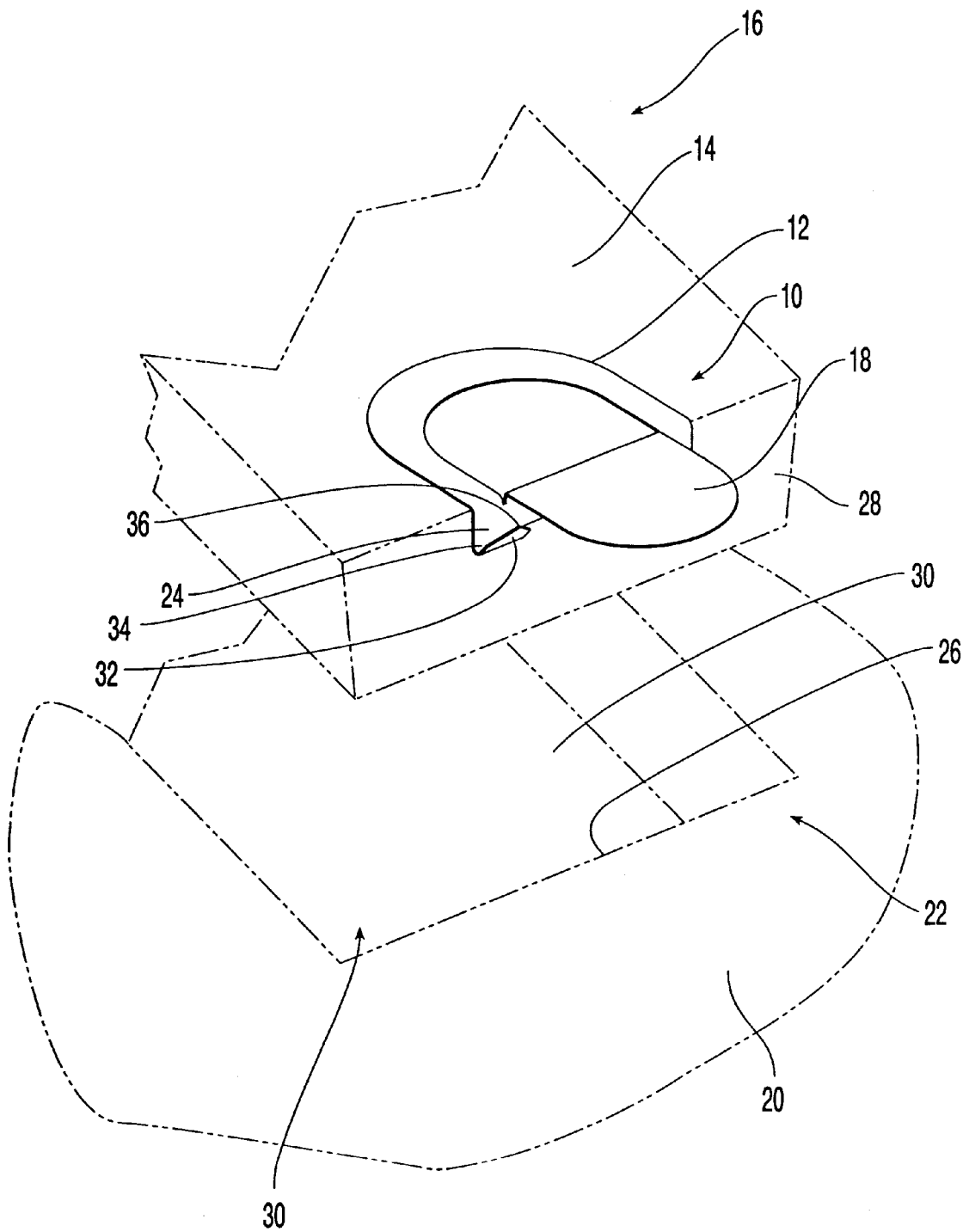
FIG. 1 is a perspective view of a first embodiment of a cranial spring clip according to the present invention.
Figure 2:
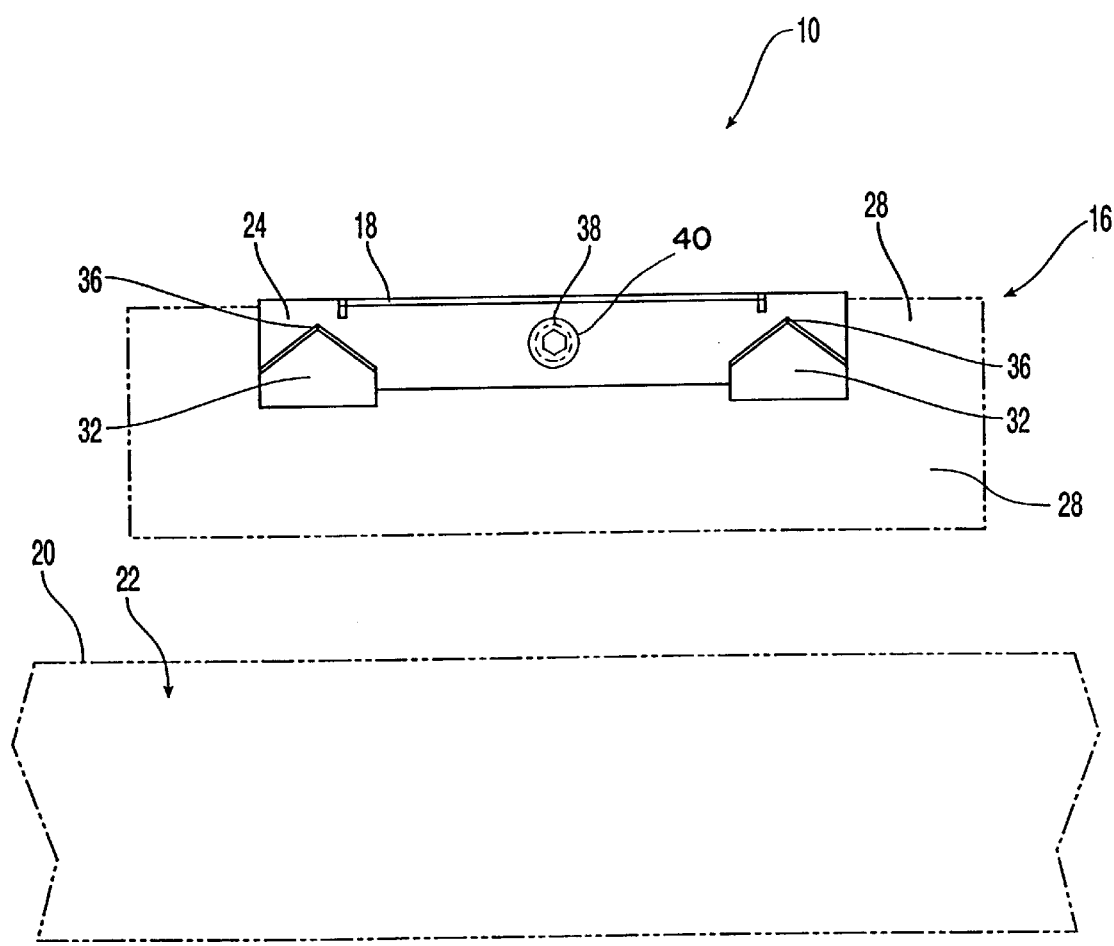
FIG. 2 is an end view of the first embodiment.

FIG. 1 and FIG. 2 show a first embodiment of the cranial spring clip 10 of the present invention just prior to the completion of implantation. Cranial spring clip 10 has a flap clipping portion 12 that is substantially flat. Upon implantation of spring clip 10, flap clipping portion 12 rests on top of a top surface 14 of bone flap 16. Cranial spring clip 10 also has a skull clipping portion 18 that is substantially flat. After implantation, skull clipping portion 18 would rest on a top surface 20 of skull 22. In anatomical terms, top surface 14 and top surface 20 are known as the outer table.

Disposed between flap clipping portion 12 and skull clipping portion 18 is extension 24. Extension 24 is substantially perpendicular to both flap clipping portion 12 and skull clipping portion 18. Extension 24 has a length that is no longer than the length of a side surface 26 of skull 22 or the length or a side surface 28 of bone flap 16. It should be noted that, within normal biological variation, the length of side surface 26 is substantially equivalent to the length of side surface 28.

A saw gap is formed by side surface 26 of skull 22 and side surface 28 of bone flap 16. Upon implantation of cranial spring clip 10, extension 24 fits in the saw gap. As the length of extension 24 is shorter than the lengths of side surface 26 and side surface 28, there is no risk of cranial spring clip 10 contacting brain 30 and causing accidental injury.

At least one burr 32 is attached to extension 24 at a base 34 of burr 32. The burr also has a shapely pointed tip 36 that extends from extension 24 at an angle. When the clip 10 is implanted, tip 36 penetrates side surface 26 of skull 22. This penetration is possible because side surface 26 is the diploe, the spongy layer between top surface 20 of skull 22 and a bottom surface (not shown) of skull 22.

In the embodiment of the cranial spring clip shown in FIG. 1 and FIG. 2, extension 24 is substantially flat. The portion of extension 24 that connects the base 34 of burr 32 is resilient in nature such that initially upon insertion of clip 10, the compressive force within the saw gap causes burr 32 to flex inward. Once the tip 36 reaches the spongy diploe surface, the resilient portion of extension 24 causes burr 32 to flex back. The resilient nature of extension 24 provides a stabilizing force that contributes to the securing of bone flap 16 to skull 22.

Extension 24 is provided with a fastening element for securing clip 10 to bone flap 16. FIG. 2 shows the fastening element as a fastener hole 38 for receiving a fastener, such as a screw 40. Alternatively, the fastening element could be a prong with a tip for penetrating the diploe. The fastening element secures clip 10 to bone flap 16 by fixing extension 24 to side surface 28 of bone flap 16. As is evident from FIG. 1 and FIG. 2, the only parts of clip 10 that protrude above top surface 14 of flap 16 and top surface 20 of skull 22 are flap clipping portion 12 and skull clipping portion 18. As flap clipping portion 12 and skull clipping portion 18 are both substantially flat, clip 10 has a low profile and the previously discussed disadvantages of known plates are minimized.

Figure 3:
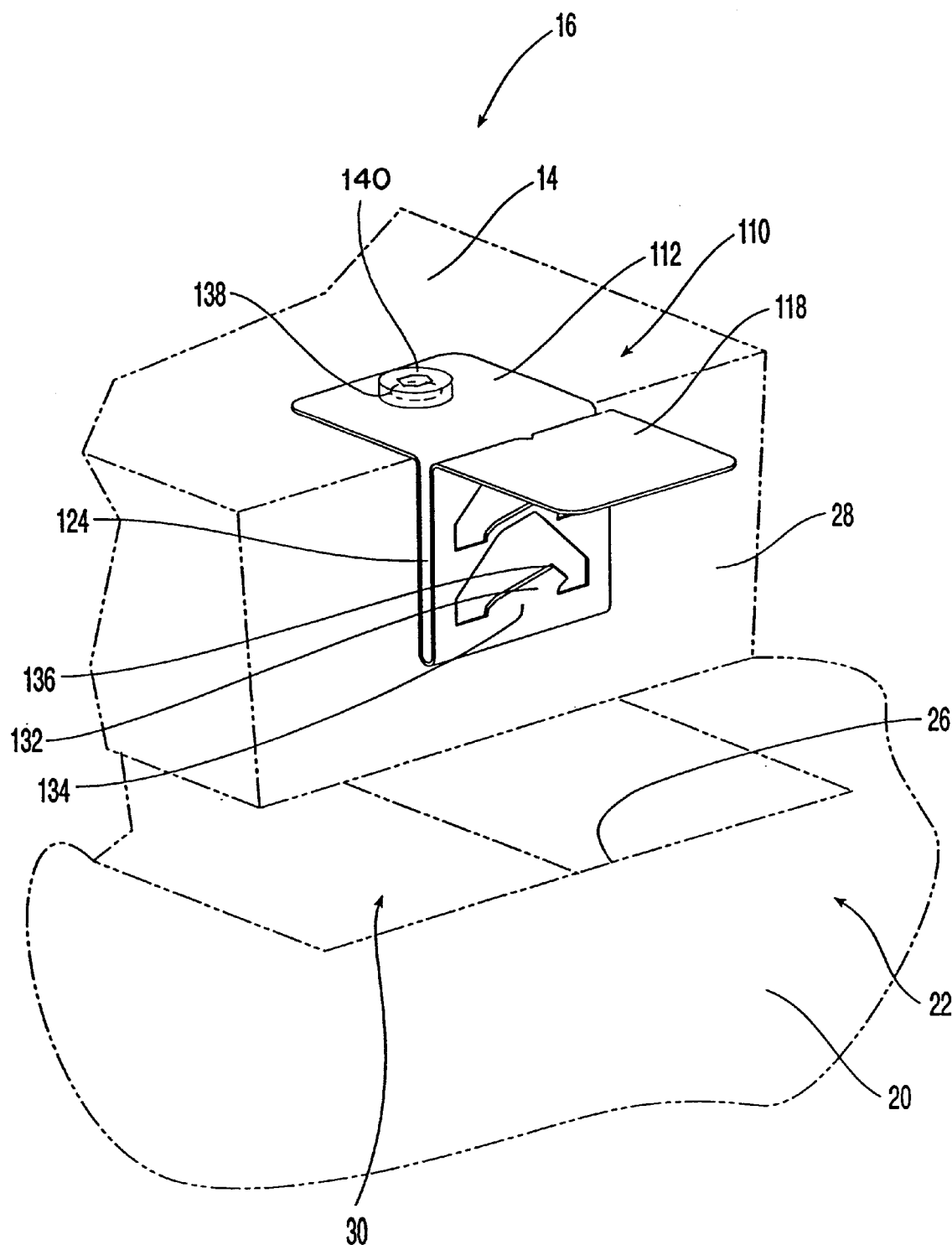
FIG. 3 is a perspective view of a second embodiment of a cranial spring clip according to the present invention.

FIG. 3 shows another embodiment of the invention. In FIG. 3, the elements of cranial spring clip 110 that are similar to the elements of cranial spring clip 10 are designated by adding 100 to the numeral used in FIG. 1 and FIG. 2. Furthermore, only those elements of clip 110 that vary from the analogous element of clip 10 are discussed in detail.

Clip 110 has an extension 124 that is "U"-shaped. Because of this shape, the curved portion of extension 124 is resilient in nature. As a result, upon initial insertion of clip 110, the compressive force within the saw gap causes extension 124 to bend such that flap clipping portion 112 and skull clipping portion 118 move towards each other. Once tips 136 of burrs 132 reach the spongy diploe surface, extension 124 flexes back and tips 136 penetrate side surface 26 of skull 22. As was the case with extension 24, extension 124 has a length that is no longer than the length of a side surface 26 of skull 22 or the length or a side surface 28 of bone flap 16.

Flap clipping portion 112 is provided with a fastening element. FIG. 3 shows one example of the fastening element: a fastener hole 138 for receiving a fastener, such as a screw 140. The fastening element secures clip 110 to bone flap 16 by fixing flap clipping portion 112 to top surface 14 of flap 16. Clip 110 is configured and arranged so that upon implantation, only a portion of the fastening element, flap clipping portion 112, and skull clipping portion 118 protrude above top surface 14 of flap 16 and top surface 20 of skull 22. As flap clipping portion 112 and skull clipping portion 118 are both substantially flat, clip 110 has a low profile and, depending on the fastening element, the above-discussed disadvantages of known plates are minimized.

Preferably, cranial spring clip 10 or cranial spring clip 110 is formed from a single piece of a material that is machined to the desired configuration. The material should be selected so that a portion of extension 24, 124 possesses the necessary resiliency. Titanium and titanium-based alloys are examples of such a material. Although flap clipping portions 12, 112 and skull clipping portions 18, 118 are shown with particular geometries, any shape can be used as long as the preferably substantially flat nature of flap is clipping portions 12, 112 and skull clipping portions 18, 118 is maintained. In practice, typically several clips 10, 110 would be used to secure bone flap 16 to skull 22. As securing clip 10, 110 to bone flap 16 requires only one fastening element, implanting clip 10, 110 is a fast and simple procedure.

While it is apparent that the illustrative embodiments of the invention herein disclosed fulfill the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

What is claimed is:

1. A cranial spring clip for fixing a bone flap to a skull to allow new bone to form therebetween, said clip comprising:

a flap clipping portion configured and dimensioned to rest on a top surface of the bone flap;

a skull clipping portion configured and dimensioned to rest on a top surface of the skull;

an extension disposed between and connecting the flap clipping portion and the skull clipping portion, and configured and dimensioned to fit between the bone flap and the skull, said extension having a length that is shorter than a skull thickness and a resilient portion that upon the application of a compressive force flexes inward and returns to its original configuration when said compressive force is removed;

at least one burr attached to the extension and having a base and a sharply pointed tip with the tip extending from the extension at an angle, said burr further configured and dimensioned to penetrate the skull; and a fastening element for securing the clip to the bone flap.

2. The spring clip of claim 1, wherein the clip is made of titanium or a titanium based alloy.

3. The spring clip of claim 1, wherein the fastening element comprises a fastener hole for receiving a fastener.

4. The spring clip of claim 1, wherein the clip is integral and comprises a cut and bent metal sheet.

5. The spring clip of claim 1, wherein the flap clipping portion is substantially flat.

6. The spring clip of claim 1, wherein the skull clipping portion is substantially flat.

7. The spring clip of claim 1, wherein the extension is substantially perpendicular to the flap clipping portion and the skull clipping portion.

8. The spring clip of claim 1, wherein the extension has a length that is shorter than the skull thickness.

9. The spring clip of claim 1, wherein the extension is substantially flat.

10. A cranial spring clip for fixing a bone flap to a skull to allow new bone to form therebetween, said clip comprising:

a flap clipping portion configured and dimensioned to rest on a top surface of the bone flap;

a skull clipping portion configured and dimensioned to rest on a top surface of the skull;

an extension disposed between and connecting the flap clipping portion and the skull clipping portion, and configured and dimensioned to fit between the bone flap and the skull, said extension having a resilient portion that upon the application of a compressive force flexes inward and returns to its original configuration when said compressive force is removed;

at least one burr attached to the extension and having a base and a tip, with the tip extending from the extension at an angle, said burr further configured and dimensioned to penetrate the skull; and a fastening element for securing the clip to the bone flap; wherein the extension is substantially U-shaped and at least two burrs of similar configuration extend from the extension.

11. The spring clip of claim 10, wherein the burrs are positioned in spaced vertical alignment.

12. A cranial spring clip for fixing a bone flap to a skull to allow new bone to form therebetween, said clip comprising:

a flap clipping portion configured and dimensioned to rest on a top surface of the bone flap;

a skull clipping portion configured and dimensioned to rest on a top surface of the skull;

an extension disposed between and connecting the flap clipping portion and the skull clipping portion, and configured and dimensioned to fit between the bone flap and the skull, said extension having a resilient portion that upon the application of a compressive force flexes inward and returns to its original configuration when said compressive force is removed;

at least one burr attached to the extension and having a base and a tip, with the tip extending from the extension at an angle, said burr further configured and dimensioned to penetrate the skull; and a fastening element for securing the clip to the bone flap, wherein the extension is substantially flat and at least two burrs of similar configuration extend from the extension.

13. The spring clip of claim 12, wherein the burrs are positioned in a spaced horizontal alignment.

14. A cranial spring clip for fixing a bone flap to a skull to allow new bone to form therebetween, said clip comprising:

a flap clipping portion configured and dimensioned to rest on a top surface of the bone flap;

a skull clipping portion configured and dimensioned to rest on a top surface of the skull;

an extension disposed between and connecting the flap clipping portion and the skull clipping portion, and configured and dimensioned to fit between the bone flap and the skull, said extension having a resilient portion that upon the application of a compressive force flexes inward and returns to its original configuration when said compressive force is removed;

at least one burr attached to the extension and having a base and a tip, with the tip extending from the extension at an angle, said burr further configured and dimensioned to penetrate the skull;

a fastener; and a fastening element for receiving the fastener and securing the clip to the bone flap.

15. The spring clip of claim 14, wherein the fastener is a screw.

16. The spring clip of claim 14, wherein the extension is substantially U-shaped.

17. The spring clip of claim 16, wherein the fastener element is located on the flap clipping portion and the fastener element has an axis substantially perpendicular to the flap clipping portion.

18. The spring clip of claim 14, wherein the extension is substantially flat.

19. The spring clip of claim 18, wherein the fastener element is located on the extension and has an axis substantially perpendicular to the extension.

* * * * *